United States Patent
Gupta et al.

(10) Patent No.: US 6,219,576 B1
(45) Date of Patent: Apr. 17, 2001

(54) PROGRAMMED ADJUSTMENT OF ELECTRIC CURRENT TO PROVIDE DESIRED ELECTRICALLY ASSISTED TRANSDERMAL DRUG DELIVERY RATE

(75) Inventors: Suneel K. Gupta, Sunnyvale; Ronald P. Haak, Palo Alto, both of CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/205,136

(22) Filed: Dec. 3, 1998

Related U.S. Application Data

(60) Provisional application No. 60/069,858, filed on Dec. 17, 1997.

(51) Int. Cl.[7] .................................................. A61N 1/30
(52) U.S. Cl. ............................................................. 604/20
(58) Field of Search .................................. 604/20, 21, 49, 604/115, 120, 149; 607/1, 2, 3, 152, 153; 606/32, 34

(56) References Cited

U.S. PATENT DOCUMENTS

| | | | |
|---|---|---|---|
| 3,991,755 | 11/1976 | Vernon et al. | 128/172.1 |
| 4,141,359 | 2/1979 | Jacobsen et al. | 128/172.1 |
| 4,250,878 | 2/1981 | Jacobsen et al. | 128/207.21 |
| 4,383,529 | 5/1983 | Webster | 604/20 |
| 4,398,545 | 8/1983 | Wilson | 128/798 |
| 4,764,164 | 8/1988 | Sasaki | 604/20 |
| 4,856,188 | 8/1989 | Sibalis | 128/641 |
| 4,886,489 | 12/1989 | Jacobsen | 604/20 |
| 4,931,046 | * 6/1990 | Newman | 604/20 |
| 4,942,883 | 7/1990 | Newman | 128/798 |
| 5,006,108 | 4/1991 | LaPrade | 604/20 |
| 5,013,293 | 5/1991 | Sibalis | 604/20 |
| 5,125,894 | 6/1992 | Phipps et al. | 604/20 |
| 5,162,042 | 11/1992 | Gyory et al. | 604/20 |
| 5,207,752 | 5/1993 | Sorenson et al. | 604/20 |
| 5,213,568 | 5/1993 | Lattin et al. | 604/20 |
| 5,314,502 | 5/1994 | McNichols | 604/20 |
| 5,387,189 | 2/1995 | Gyory | 604/20 |
| 5,421,817 | 6/1995 | Liss et al. | 604/20 |
| 5,427,585 | * 6/1995 | Bettinger | 604/20 |
| 5,498,235 | 3/1996 | Flower | 604/20 |
| 5,622,530 | 4/1997 | Phipps | 604/20 |
| 5,676,648 | 10/1997 | Henley | 604/20 |
| 5,688,232 | 11/1997 | Flower | 604/20 |
| 5,695,459 | 12/1997 | Meguro | 604/20 |
| 5,857,994 | * 1/1999 | Flower | 604/20 |
| 5,865,786 | * 2/1999 | Sibalis et al. | 604/20 |
| 6,029,083 | * 2/2000 | Flower et al. | 604/20 |

FOREIGN PATENT DOCUMENTS

| | | | |
|---|---|---|---|
| WO 86/07269 | 12/1986 | (WO) | A61N/1/30 |
| WO 88/08729 | 11/1988 | (WO) | A61N/1/30 |
| WO 91/15258 | 10/1991 | (WO) | A61N/1/30 |
| WO 92/18197 | 10/1992 | (WO) | A61N/1/30 |
| WO 97/07854 | 3/1997 | (WO) | A61N/1/30 |

\* cited by examiner

*Primary Examiner*—Sharon Kennedy
(74) *Attorney, Agent, or Firm*—Owen J. Bates; Steven F. Stone

(57) ABSTRACT

The present invention is an apparatus and method that maintains a constant drug delivery rate for an electrotransport delivery system, while the apparent transport efficiency of the system varies, by making adjustments to the output current of the system. More specifically, the constant drug delivery rate is maintained by the regulator of the electrotransport delivery system automatically adjusting the output current to compensate for the varying apparent transport efficiency.

35 Claims, 2 Drawing Sheets

PROGRAMMED ADJUSTMENT OF ELECTRIC CURRENT TO PROVIDE DESIRED ELECTRICALLY ASSISTED TRANSDERMAL DRUG DELIVERY RATE

RELATED APPLICATIONS

This application claims the benefit of U.S. Provisional Application No. 60/069,858, filed Dec. 17, 1997.

TECHNICAL FIELD OF THE INVENTION

The present invention relates generally to an electrotransport delivery system (hereinafter "ETS") for transdermally or transmucosally delivering a beneficial agent (e.g., a drug) to a patient. More particularly, the present invention relates to a portable or patient-worn ETS having an automated delivery regulator that electrically compensates for any variation in the apparent transport efficiency of the device, in order to provide a desired drug delivery rate.

BACKGROUND OF THE INVENTION

The term "electrotransport" as used herein refers generally to the delivery of an agent (e.g., a drug) through a membrane, such as skin, mucous membrane, or nails. The drug delivery is at least partially induced or aided by the application of an electric potential. For example, a beneficial therapeutic agent may be introduced into the systemic circulation of an animal (e.g., a human) by electrotransport delivery through the skin.

The electrotransport process has been found to be useful in the transdermal administration of drugs including lidocaine hydrochloride, hydrocortisone, fluoride, penicillin, dexamethasone sodium phosphate, and many other drugs. Perhaps the most common use of electrotransport is in diagnosing cystic fibrosis by delivering pilocarpine salts iontophoretically. The pilocarpine stimulates the production of sweat; the sweat is collected and analyzed for its chloride content to detect the presence of the disease.

Presently known electrotransport systems use at least two electrodes, positioned in intimate contact with some portion of the animal's body (e.g. the skin). A first electrode, called the active or donor electrode, delivers the therapeutic agent (e.g. a drug or a prodrug) into the body by electrotransport. The second electrode, called the counter or return electrode, closes an electrical circuit with the first electrode through the animal's body. A source of electrical energy, such as a battery, supplies electric current to the body through the electrodes. For example, if the therapeutic agent to be delivered into the body is positively charged (i.e., a cation), the anode will be the active electrode and the cathode will serve as the counter electrode to complete the circuit. If the therapeutic agent to be delivered is negatively charged (i.e., an anion), the cathode will be the donor electrode and the anode will be the counter electrode.

Alternatively, both the anode and cathode may be used to deliver drugs of opposite electrical charge into the body. In this situation, both electrodes are considered donor and counter electrodes. For example, the anode can simultaneously deliver a cationic therapeutic agent and act as a "counter" electrode to the cathode. Similarly, the cathode can simultaneously deliver an anionic therapeutic agent into the body and act as a "counter" electrode to the anode.

A widely used electrotransport process, electromigration (also called iontophoresis), involves the electrically induced transport of charged ions. Another type of electrotransport, electroosmosis, involves the electrically facilitated flow of a liquid solvent either from the donor electrode to the counter electrode or from the counter electrode to the donor electrode, under the influence of the applied electric field.

Still another type of electrotransport process, electroporation, involves the formation of transiently existing pores in a biological membrane by the application of high voltage pulses. A therapeutic agent can in part be delivered through the skin by passive diffusion by reason of the concentration difference between the concentration of the drug in the donor reservoir of the ETS and the concentration of the drug in the tissues of the animal's body. In any given electrotransport process, more than one of these processes may be occurring simultaneously to a certain extent.

Accordingly, the term "electrotransport", as used herein, should be given its broadest reasonable possible interpretation so that it includes the electrically induced or enhanced transport of at least one therapeutic agent, whether charged, uncharged, or a mixture thereof. Further, the terms load current and the current flowing through the skin are defined as the current flowing between the two electrodes.

Electrotransport systems generally require a reservoir or source of the agent, or a precursor of such agent, that is to be delivered into the body by electrotransport. Examples of such reservoirs or sources of, preferably ionized or ionizable, agents include a pouch as described in Jacobsen U.S. Pat. No. 4,250,878, or a pre-formed gel body as disclosed in Webster U.S. Pat. No. 4,383,529. Such reservoirs are electrically connected to the anode or the cathode of an ETS to provide a fixed or renewable source of one or more desired therapeutic species.

Recently, a number of U.S. Patents have issued in the electrotransport field, indicating a continuing interest in this mode of drug delivery. For example, Vernon et al U.S. Pat. No. 3,991,755, Jacobsen et al U.S. Pat. No. 4,141,359, Wilson U.S. Pat. No. 4,398,545, Jacobsen U.S. Pat. No. 4,250,878, Sorenson et al. U.S. Pat. No. 5,207,752, Lattin et al. U.S. Pat. No. 5,213,568, and Flower U.S. Pat. No. 5,498,235 disclose examples of electrotransport systems and some applications thereof. All of the above mentioned patents are hereby incorporated in their entirety by reference.

More recently, electrotransport delivery systems have become much smaller, particularly with the development of miniaturized electrical circuits (e.g., integrated circuits) and more powerful lightweight batteries (e.g., lithium batteries). The advent of inexpensive miniaturized electronic circuitry and compact, high-energy batteries has meant that the entire system can be made small enough to be unobtrusively worn on the skin of the patient and under clothing. This allows the patient to remain fully ambulatory and able to perform all normal activities, even during periods when the electrotransport system is actively delivering a drug.

However, some disadvantages still remain in the ETS prior art that restrict the wider application of ETS devices. One such disadvantage is the difficulty in regulating the rate of drug delivery to the user of the ETS when the apparent transport efficiency of the ETS for the drug in use is not constant. (The term "apparent transport efficiency", hereinafter "ATE", refers to a measurement of the amount of drug delivered for a unit time period by an "ETS". More specifically, the ATE of an ETS for a drug in use is equal to the amount of the drug delivered per unit time period divided by the average electrical current output over that time period by the ETS. Herein, the "average electrical current" is the average current flowing between two electrodes of the ETS.)

The ATE of an ETS for a drug may vary as a function of time or as function of other parameters, such as the pH level of the donor electrode, when maintenance of a constant drug delivery rate is required. For example, in the case of the fentanyl-on-demand ETS, it is normally necessary that all doses delivered to the user in any time period during the application period be equal, so that the patient gets the same relief after each dose. If the drug delivery rate is not properly regulated, then a serious overdose or underdose situation may result. However, under certain conditions, the ATE of fentanyl delivered by an ETS appears to vary substantially during delivery by the ETS, making problematic the delivery of fentanyl by a prior art ETS at a constant rate.

Stabilization of the ATE of some drugs to humans appears to occur rapidly, facilitating their delivery by prior art ETS technology. For example, several pilot clinical studies involving electrically assisted transdermal delivery of metoclopramide have repeatedly shown that the ATE for this drug appears to stabilize within an hour of application.

However, in certain applications, e.g., the demand delivery of fentanyl under certain conditions, the ATE of prior art ETS devices varies, preventing maintenance of the drug delivery rate within an acceptable range with prior art ETS devices.

Hence, there is a need for an improved ETS that maintains a constant drug delivery rate when the ATE varies.

SUMMARY OF THE INVENTION

The present invention overcomes the above discussed disadvantages of the prior art. The present invention is an apparatus and method that maintains a constant drug delivery rate for an ETS while the ATE varies. More specifically, the constant drug delivery rate is maintained by the regulator of the ETS of the present invention automatically adjusting the output current to compensate for a varying ATE.

It will be shown that the first task in delivering a desired level of a drug using a ETS is to obtain an accurate model of the ATE profile which varies with a particular parameter or parameters. Once an accurate ATE model is obtained, then the required average output current profile (that is, average output current varied over time) is calculated to maintain a constant drug delivery rate. The present invention automatically adjusts the output current, or time of current application in certain applications such as on-demand dosing, to match the output current profile needed to maintain the target drug delivery rate for the selected ATE model.

DETAILED DISCLOSURE OF THE INVENTION

I. Apparent Transport Efficiency

As a first step in delivering a desired level of a drug using an ETS, an accurate model of the ATE profile of the drug must be obtained.

Figure 2:
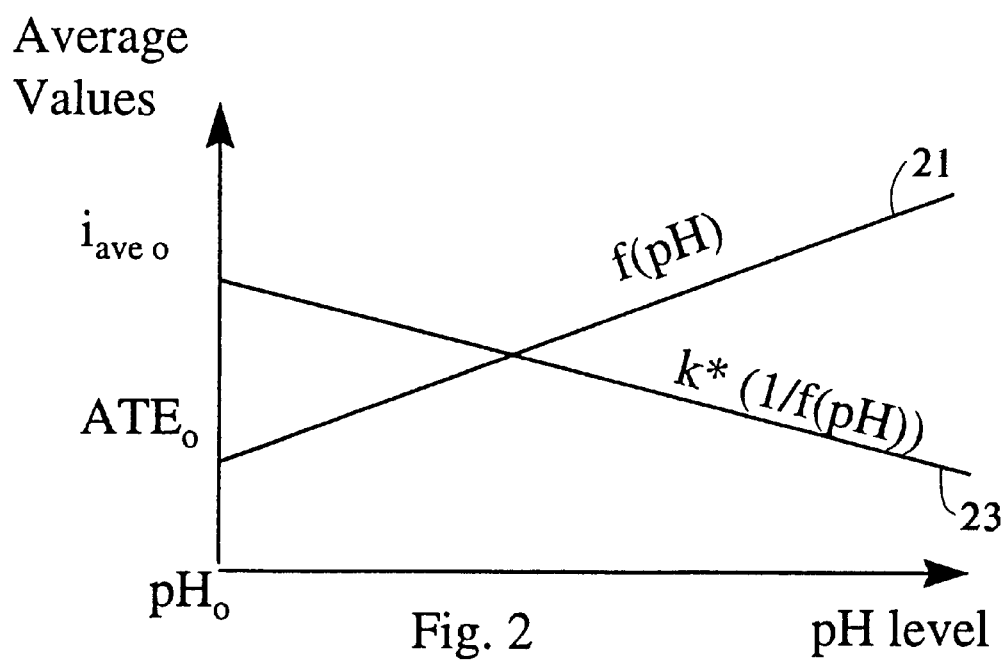
FIG. 2 is a plot of ATE and $i_{avg}$ for a constant drug delivery rate when the ATE is a linearly increasing function of pH level.
Figure 3:
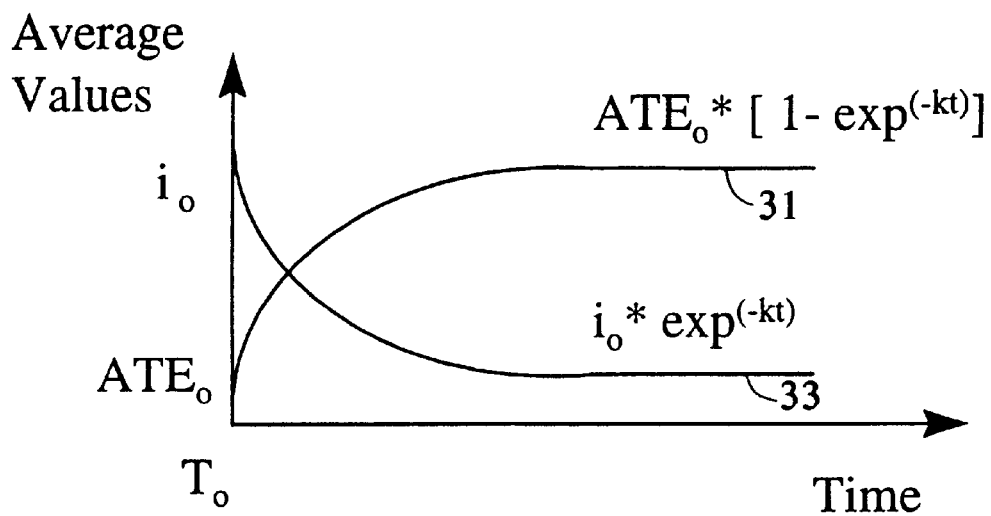
FIG. 3 is a time line plot of ATE and $i_{avg}$ for a constant drug delivery rate when the ATE is exponentially increasing function of time.

The amount of drug delivered from an ETS, and the ATE for an ETS, are determined primarily by electrical charge, current density, and donor electrode formulation of the ETS. When the ATE is evaluated as a function of application time, the kinetics of stabilization can sometimes be quite rapid, e.g., for metoclopramide. In the case of other drugs, such as fentanyl electrotransport under certain conditions, the ATE may take longer to stabilize. A variety of ATE models which take longer to stabilize are illustrated in FIGS. 1–3.

ATE Model 1

Figure 1:
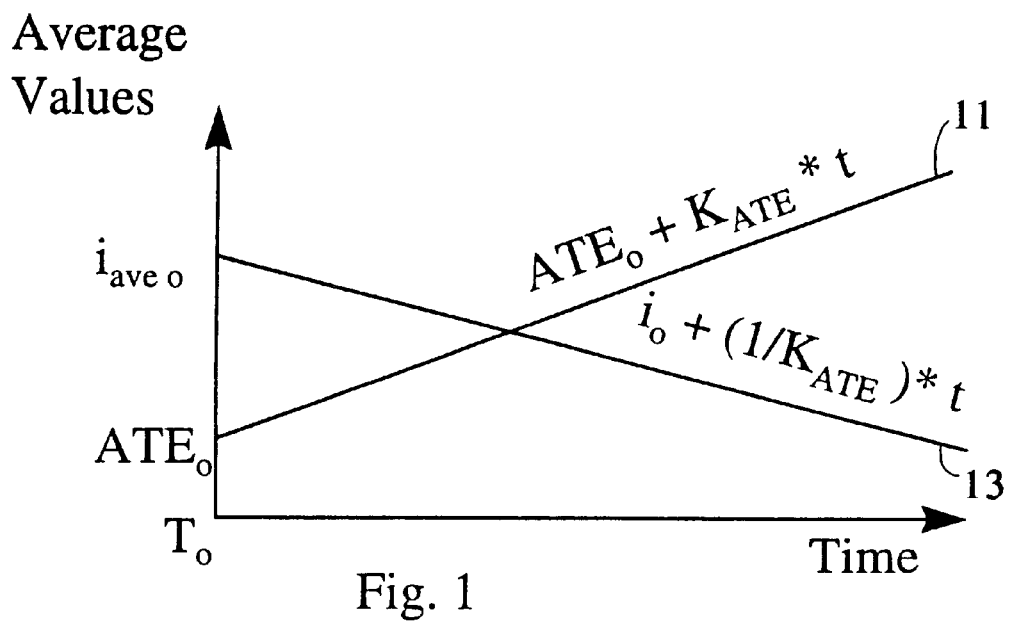
FIG. 1 is a time line plot of an ATE and $i_{avg}$ (average load current) for a constant drug delivery rate when the ATE is a linearly increasing function of time.

FIG. 1 shows the simplest ATE profile model, which is a linearly increasing function of time. More specifically, the ATE profile for a particular drug that increases linearly with time (t) can be modeled as:

$$ATE(t)=ATE_o+K_{ATE}*t \qquad \text{Eq. (1)}$$

where $ATE_o$ is the ATE at the start of the application time and $K_{ATE}$ is a proportionality constant. Eq. (1) is depicted by a constantly increasing line 11 in FIG. 1. This means as time increases, the efficiency of delivering the drug (the ATE) increases, requiring less load current to supply the same amount of drug.

ATE Model 2

In addition to the ATE varying as a linear function of time, it can also be function of other parameters. For example, in some cases of fentanyl on-demand ETS, the ATE could change as a function of the number of doses delivered. Likewise, pH of the donor electrode, which could change as a function of discharge time, could alter the ATE. Hence, if the ATE varies with the pH of the donor electrode, the relationship can be formulated as:

$$ATE(pH)=ATE_o+K_{ATE}*pH \qquad \text{Eq. (2)}$$

A constantly increasing line 21 in FIG. 2 depicts the ATE as a function of the pH level. However, the ATE can be linearly decreasing function or it can also be a non-linear function of the pH level. The following is an example of an ATE function that has non-linear characteristics.

ATE Model 3

In some cases of the electrically assisted transdermal delivery of fentanyl, using a direct current of 0.01–0.1 mA/cm$^2$, the ATE appears to require some amount of time to stabilize. For example, in one pilot clinical study involving a particular formulation of fentanyl, a current of 0.1 mA/cm$^2$, an electrode area of 2 cm$^2$, and a 24 h application period, the ATE at hour 12 was about 200% that of the rate at hour one. Between hours 12 and 24 the increase was only about 10%.

Therefore, the preceding study indicates for some formulations of fentanyl, the ATE could be modeled as a increasing function of the following equation:

$$ATE=ATE_o*(1-\exp^{(-KAT2*t)}) \qquad \text{Eq. (3)}$$

where KAT2 represents a second proportionality constant. This Eq. (3) is depicted by a curve 31 in FIG. 3. In addition to an exponentially increasing ATE function, other non-linear ATE functions are contemplated within this invention.

In general, ATE is a function of many parameters, e.g., time, pH level, number of doses applied, and competing ions, that is:

$$ATE=f(a, b, c, \ldots) \qquad \text{Eq. (4)}$$

This is a general function which could be a linear or non-linear function of the parameters.

II. Obtaining the desired $I_{avg}$

The total amount of drug delivered (AMT), is directly proportional to ATE multiplied by the average current ($i_{avg}$), i.e., $$AMT=ATE*i_{avg}*K \qquad \text{Eq. (5)}$$

where K is an empirically derived proportionality constant. Eq. (5) shows that when the ATE and K are known, the desired level of AMT is maintained by appropriately adjusting current to a desired $i_{avg}$. The desired $i_{avg}$ is also referred to as the sought load current. Further, Eq. (5) indicates that the $i_{avg}$ and ATE are inversely proportional to each other to maintain a constant AMT. Hence, in order to maintain a constant level of delivery, $i_{avg}$ must decrease when the ATE is increasing, and $i_{avg}$ must increase when the ATE is decreasing.

Therefore, as a second step in delivering a desired level of a drug using an ETS, an accurate model of the desired $i_{avg}$ of a drug is required.

Under the ATE Model 1, $i_{avg}$ must be adjusted with the same proportionality, i.e.:

$$i_{avg}(t)=i_o-K_{ATE}*t \qquad \text{Eq. (6)}$$

where $i_o$ is the initial average current. The above equation is depicted by a linearly decreasing line 13 of FIG. 1. The rate of decrease of the $i_{avg}$ must equal to the rate of increase of the ATE to make the AMT constant over time.

Under ATE Model 2, if the functionality between the pH and ATE is understood and if a sensor in the donor electrode indicates that the pH has shifted, then $i_{avg}$ can be adjusted to maintain the delivery rate within performance specifications according to the relationship:

$$i_{avg}(\text{pH})=I_o-K_{ATE}*\text{pH} \qquad \text{Eq. (7)}$$

A linearly decreasing line 23 in FIG. 2 depicts the above equation. Similar to the embodiment under ATE Model 1, the $i_{avg}(\text{pH})$ is inversely proportional to ATE(pH) in order to maintain a constant AMT level.

In this embodiment, the sensor determines the shifting pH levels, but, in other embodiments contemplated within this invention, the sensor can also determine the dosage level that already have been delivered by the ETS, the level of instantaneous current and/or voltage, the resistance of treated skin or any other parameters that helps to generate the appropriate adjustments to $i_{avg}$.

Under the ATE model 3, the $i_{avg}$ needs to be decreased as follows:

$$i_{avg}(t)=i_o*\exp^{(-kAT2*t)} \qquad \text{Eq. (8)}$$

to maintain a constant AMT. This is shown as curve 33 in FIG. 3.

However, under certain other situations, the fentanyl ATE varies as a function of time, such that if a constant AMT is desired, then, $i_{avg}$ needs to be increased as follows:

$$i_{avg}(t)=i_o*(1-\exp^{(-kAT2*t)}) \qquad \text{Eq. (9)}$$

Finally, for any general ATE function as depicted in Eq. (4), a desired $i_{avg}$ function is obtained in accordance with the general function to maintain a constant AMT.

III. Load Current $i_L$

Figure 4:
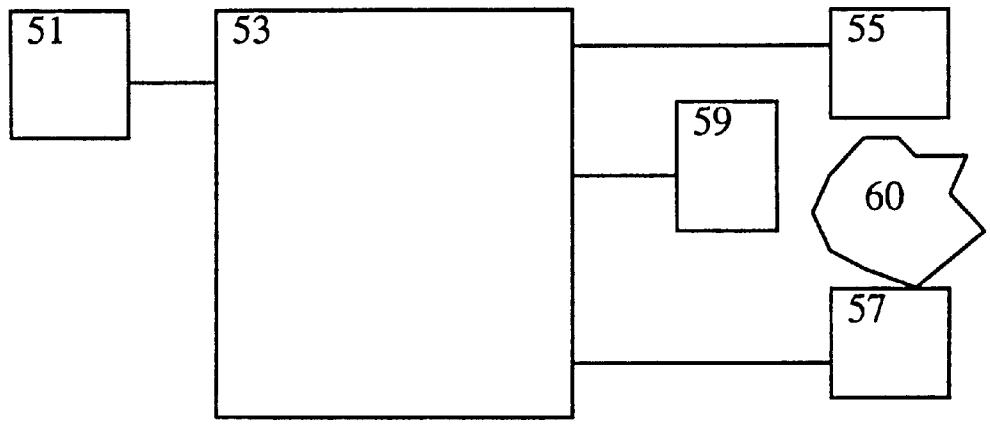
FIG. 4 is a block schematic of an preferred exemplary embodiment of a regulator.

Once the desired $i_{avg}$ is determined, then an ETS is implemented to regulate the load current, $i_L$, to generate the desired $i_{avg}$. A regulator within the ETS generates a load current, $i_L$, in accordance with a predetermined load current pattern. FIG. 4 depicts an exemplary preferred embodiment of such an ETS including an electrical power source 51, a regulator 53, a sensor 59, and a pair of electrodes 55 and 57.

The external electrical power source 51 is preferably a light weight portable battery being connected to regulator 53, but power source 51 can also be a number of batteries being connected individually to regulator 53.

Regulator 53 receives its electrical power from power source 51 and supplies the load current $i_L$ flowing between electrodes 55 and 57 in accordance with a predetermined load current pattern. The load current flows from electrode 55 through the treated skin 60 and to electrode 57. Reservoir(s) of drug is attached to either or both of electrodes 55 and 57. Regulator 53 also receives sensed information from sensor 59, but regulator 53 is capable of operating with or without sensor 59.

In an exemplary embodiment of regulator 53 supplying the load current $i_L$ for the ATE Model 2 described above, sensor 59 determines the pH level of electrode 55. However, sensor 59 can be connected to other devices or skin surfaces to determine the dosage level that already has been delivered by the ETS, the level of instantaneous current and/or voltage, the resistance of treated skin or any other parameters.

In an exemplary preferred embodiment, the regulator is implemented with a micro-controller, microprocessor, or other programmable electronic devices or by any means possible as known by person skilled in the art of electrical circuitry design. The desired average load current $I_{avg}$, is then downloaded from an external processor to the regulator. This embodiment can be used where a patient brings his/her ETS to a doctor who has an ETS programmer. When the doctor prescribes a drug to be administered to the patient with the ETS, then the doctor downloads appropriate $I_{avg}$ function to the ETS from the ETS programmer. The ETS, then, selects and generates appropriate load current, $i_L$, pattern from the downloaded $I_{avg}$. In the alternative, the load current $i_L$ pattern is directly downloaded allowing the ETS to skip the step of calculating the load current $i_L$ pattern from a down loaded $I_{avg}$.

In another exemplary embodiment, the $I_{avg}$ functions are previously stored to the ETS. The patient or the doctor then selects an appropriate $i_{avg}$ function from the previously stored functions. In the alternative, the load current $i_L$ patterns are stored in the ETS allowing the patient or the doctor to select an appropriate load current $i_L$ pattern directly.

In yet another exemplary embodiment, the regulator inside an ETS is implemented with interchangeable circuit boards or components with one or more load current $i_L$ patterns implemented in each of the interchangeable circuits. The patient or the doctor can then insert an appropriate interchangeable board or component for a specific drug to be administered.

A more detailed description of the load current pattern is provided herein. If the load current, $i_L$, is a direct current, the generated load current pattern makes adjustments to the load current $i_L$ by changing the level of the load current.

In another embodiment, if the load current $i_L$ is a pulsed (square wave) current, the generated load current pattern makes adjustments to the load current $i_L$ either by changing the magnitude or by changing the duty cycle of the $i_L$ pulse. For example, an $I_{avg}$ of a 0–0.05 mA/cm$^2$, 10% duty cycle pulse is 0.005 mA/cm$^2$. For the purpose of this embodiment, it is stipulated that the frequency is less than 100 Hz. Doubling the preceding $i_{avg}$ is accomplished by increasing the load current, $i_L$, to 0–0.1 mA/cm$^2$ while keeping the duty cycle constant at 10%, or doubling the duty cycle to 20% while maintaining the load current, $i_L$, at 0–0.05 mA/cm$^2$. (Note that these relationships are approximations.) If other modulated current is used, the load current, $i_L$, can be changed by changing the shape of the waveform. In the case of direct current or pulsed current, the total time of current application could also be adjusted in order to provide a desired agent delivery rate, particularly in on-demand delivery applications.

In another embodiment, the voltage supplied across electrodes 55 and 57 is controlled by regulator 53 to achieve the desired $i_{avg}$. This is possible because the load voltage and the load current, $i_L$, between two electrodes 55 and 57 follow the Ohm=s law (voltage=current*resistance), hence the load current is regulated by regulating the load voltage when the skin resistance is known by the sensor.

These methods can be implemented using the approaches described above. Electrical current waveforms or output voltages (which in turn control output current) can be controlled by pre-programming circuit elements, such as processors or controllers, or by changing components or boards.

Any agent may be used, so long as it is at least partly ionized. The terms "drug" and "agent" are used herein interchangeably and are intended to have their broadest reasonable interpretation, namely any therapeutically active substance that is delivered to a living organism to produce a desired, usually beneficial, effect. For example, the terms "drug" and "agent" include therapeutic compounds and molecules from all therapeutic categories including, but not limited to, anti-infectives (such as antibiotics and antivirals), analgesics (such as fentanyl, sufentanil, buprenorphine, and analgesic combinations), anesthetics, antiarthritics, antiasthmatics (such as terbutaline), anticonvulsants, antidepressants, antidiabetics, antidiarrheals, antihistamines, anti-inflammatories, antimigranes, antimotion sickness preparations (such as scopolamine and ondansetron), antineoplastics, antiparkinsonisms, antipruritics, antipsychotics, antipyretics, antispasmodics (including gastrointestinal and urinary), anticholinergics, sympathomimetrics, xanthine and derivatives thereof, cardiovascular preparations (including calcium channel blockers such as nifedipine, beta-agonists (such as dobutamine and ritodrine), beta blockers, antiarrythmics, antihypertensives (such as atenolol), ACE inhibitors (such as lisinopril), diuretics, vasodilators (including general, coronary, peripheral and cerebral), central nervous system stimulants, cough and cold preparations, decongestants, diagnostics, hormones (such as parathyroid hormones), hypnotics, immunosuppressives, muscle relaxants, parasympatholytics, parasympathomimetrics, prostaglandins, proteins, peptides, psychostimulants, sedatives and tranquilizers.

More preferably, the electrotransport device of the present invention delivers drugs and/or agents including baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine and verapamil.

Preferably, the electrotransport device of the present invention may also deliver peptides, polypeptides, proteins and other macromolecules. Such molecules are known in the art to be difficult to deliver transdermally or transmucosally due to their size. For example, such molecules may have molecular weights in the range of 300–40,000 daltons and include, but not limited to, LHRH and analogs thereof (such as buserelin, gosserelin, gonadorelin, naphrelin and leuprolide), GHRH, GHRF, insulin, insulinotropin, heparin, calcitonin, octreotide, endorphin, TRH, NT-36 or N-[[(s)-4-oxo-2-azetidinyl]carbonyl]L-histidyl-L-prolinamide], liprecin, pituitary hormones (such as HGH, HMG, HCG, desmopressin acetate), follicile luteoids, a-ANF, growth factor releasing factor (GFRF), b-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (such as urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1 antitrypsin (recombinant), and TGF-beta.

Although the invention has been described above with respect to its preferred form, those with skill in the art will readily recognize that various modifications and changes may be made hereto without departing from the spirit and scope of the claims appended hereto.

We claim:

1. A method of regulating an electrotransport system delivering a beneficial agent by supplying a load current across a first electrode and a second electrode, the method comprising the steps of:

(a) generating a load current in accordance with a load current pattern; and (b) supplying the generated load current to the electrodes, wherein the supplied load current achieves a sought load current which is inversely proportional to an apparent transport efficiency of the beneficial agent when a constant beneficial agent delivery rate is maintained, (c) wherein the apparent transport efficiency of the beneficial agent is $$ATE_o*(1-\exp^{(-K_{ATE}*t)})$$

and the desired average current is $$i_o*\exp^{(-K_{ATE}*t)}$$

where $ATE_o$ and $i_o$ are an initial apparent transport efficiency and an initial sought load current, respectively, $K_{ATE}$ is a rate constant, and t is time, (d) wherein the load current is a pulsed current and the load current is adjusted by adjusting one of the magnitude, time, and the duty cycle of the pulse, and (e) wherein the method is implemented in an interchangeable circuit board or component.

2. A method of regulating an electrotransport system delivering a beneficial agent by supplying a load current across a first electrode and a second electrode using an electrical power source, the method comprising the steps of:

generating an initial load current necessary to provide a sought beneficial agent delivery rate; and varying the load current to maintain a sought beneficial agent delivery rate as an apparent transport efficiency changes.

3. The method according to claim 2, wherein the apparent transport efficiency of the beneficial agent linearly increases with time and the sought load current linearly decreases with time.

4. The method according to claim 3, wherein the apparent transport efficiency of the beneficial agent is $$ATE_o+K_{ATE}*t$$

and the sought load current is $$i_o-K_{ATE}*t$$

where $ATE_o$ and $i_o$ are an initial apparent transport efficiency and the initial load current, respectively, t is time and $K_{ATE}$ is a proportionality constant.

5. The method according to claim 2, wherein the apparent transport efficiency of the beneficial agent and the sought load current change with the pH level of one of the electrodes.

6. The method according to claim 2, wherein the apparent transport efficiency of the beneficial agent and the sought load current change non-linearly with time.

7. The method according to claim 6, wherein the apparent transport efficiency of the beneficial agent is $$ATE_o * (1-\exp^{(-KATE*t)})$$

and the sought load current is $$i_o * \exp^{(-KATE*t)}$$

where $ATE_o$ and $i_o$ are an initial apparent transport efficiency and the initial load current, respectively, $K_{ATE}$ is a rate constant, and t is time.

8. The method according to claim 2, wherein the load current is a direct current, and the load current is adjusted to the level of the sought load current.

9. The method according to claim 2, wherein the load current is a pulsed current, and the load current is adjusted by one of the magnitude, time, and the duty cycle of the pulses.

10. The method according to claim 2, wherein a pattern of the sought load current is downloaded externally.

11. The method according to claim 2, wherein a pattern of sought load current is selectable from one of a linear function of time, a non-linear function of time, and a function of the pH level of one of the electrodes.

12. The method according to claim 2, wherein a pattern of the load current is selectable from one of:

(a)

$$i_o - K_{ATE} * t$$

where $i_o$ is the initial load current and $K_{ATE}$ is a rate constant;

(b)

$$i_o * \exp^{(-KATE*t)}$$

where $i_o$ is the initial load current, $K_{ATE}$ is a rate constant, and t is time; and (c) function of the pH level of one of the electrodes.

13. The method according to claim 2, wherein the load current is one of:

(a) a direct current which is adjusted to the level of the sought load current; and (b) a pulsed current which is adjusted by one of the magnitude and the duty cycle of the pulses.

14. The method according to claim 2, wherein the method is implemented in one of a microcontroller and microprocessor.

15. The method according to claim 2, wherein the method is implemented by an interchangeable circuit board or component.

16. The method according to claim 2, wherein the sought beneficial agent delivery rate is maintained substantially constant by automatically adjusting the load current while an apparent transport efficiency varies.

17. The method according to claim 16, wherein the agent is fentanyl.

18. An electrotransport apparatus delivering a beneficial agent, the electrotransport apparatus comprising:

(a) a first electrode;

(b) a second electrode;

(c) a power source electrically connected with the electrodes;

(d) a regulator regulating the power source; and (e) at least one beneficial agent reservoir associated with an electrode, wherein the regulator generates an initial load current necessary to provide a sought beneficial agent delivery rate and varies the load current to maintain a sought beneficial agent delivery rate as an apparent transport efficiency changes.

19. The apparatus according to claim 18, wherein the apparent transport efficiency of the beneficial agent linearly increases with time and the sought load current linearly decreases with time.

20. The apparatus according to claim 18, wherein the apparent transport efficiency of the beneficial agent and the sought load current change with the pH level of one or both of the electrodes.

21. The apparatus according to claim 18, wherein the apparent transport efficiency of the beneficial agent and the sought load current change non-linearly with time.

22. The apparatus according to claim 18, wherein the load current is a direct current, and the load current is adjusted to the level of the sought load current.

23. The apparatus according to claim 18, wherein the load current is a pulsed current, and the load current is adjusted by one of the magnitude, time, and the duty cycle of the pulses.

24. The apparatus according to claim 18, wherein a pattern of the sought load current is downloaded externally.

25. The apparatus according to claim 18, wherein a pattern of sought load current is selectable from one of a linear function of time, a non-linear function of time, and a function of the pH level of one of the electrodes.

26. The apparatus according to claim 18, wherein a pattern of the load current is selectable from one of:

(a) $i_o - K_{ATE} * t$ where $i_o$ is the initial load current and $K_{ATE}$ is a proportionality constant;

(b) $i_o * \exp^{(-KATE*t)}$ where $i_o$ is the initial load current, $K_{ATE}$ is a proportionality constant, and t is time; and (c) function of the pH level of one of the electrodes.

27. The apparatus according to claim 18, wherein the load current is one of:

(a) a direct current which is adjusted to the level of the sought load current; and (b) a pulsed current which is adjusted by one of the magnitude and the duty cycle of the pulses.

28. The apparatus according to claim 18, wherein the apparatus is implemented using one of a microcontroller and microprocessor.

29. The apparatus according to claim 18, wherein the apparatus is implemented using an interchangeable circuit board.

30. The apparatus according to claim 18, wherein the sought beneficial agent delivery rate is maintained substantially constant by automatically adjusting the load current while an apparent transport efficiency varies.

31. The method according to claim 30, wherein the agent is fentanyl.

32. A method of regulating an electrotransport system delivering a beneficial agent by supplying a load current across a first electrode and a second electrode using an electrical power source, the method comprising the steps of:

generating an initial load current necessary to provide a sought beneficial agent delivery rate; and varying the load current to maintain a sought beneficial agent delivery rate as an apparent transport efficiency increases linearly with time wherein the apparent transport efficiency of the beneficial agent is $$ATE_0 + K_{ATE} * t$$

And the sought load current is $$i_0 - K_{ATE} * t$$

where $ATE_0$ and $i_0$ are an initial apparent transport efficiency and the initial load current, respectively, t is time and $K_{ATE}$ is a proportionality constant.

33. A method of regulating an electrotransport system delivering a beneficial agent by supplying a load current across a first electrode and a second electrode using an electrical power source, the method comprising the steps of:

generating an initial load current necessary to provide a sought beneficial agent delivery rate; and varying the load current to maintain a sought beneficial agent delivery rate as an apparent transport efficiency increases non-linearly with time wherein the apparent transport efficiency of the beneficial agent is $$ATE_0 * (1-\exp^{(-K_{ATE}*t)})$$

And the sought load current is $$i_0 * \exp^{(-K_{ATE}*t)}$$

wherein $ATE_0$ and $i_0$ are an initial apparent transport efficiency and the initial load current, respectively, t is time and $K_{ATE}$ is a proportionality constant.

34. A method of regulating an electrotransport system delivering a beneficial agent by supplying a load current across a first electrode and a second electrode using an electrical power source, the method comprising the steps of:

generating an initial load current necessary to provide a sought beneficial agent delivery rate; and varying the load current to maintain a sought beneficial agent delivery rate as an apparent transport efficiency changes with time, wherein the pattern of the change in said apparent transport efficiency is selected from the group consisting of (a) $i_0 - K_{ATE}*t$, where $i_0$ is the initial load current and $K_{ATE}$ is a rate constant;

(b) $i_0 * \exp^{(-K_{ATE}*t)}$, where $i_0$ is the initial load current, $K_{ATE}$ is a rate constant, and t is time; and (c) function of the pH level of one of the electrodes.

35. An electrotransport apparatus for delivering a beneficial agent, the electrotransport apparatus comprising:

(a) a first electrode;

(b) a second electrode;

(c) a power source electrically connected with the electrodes;

(d) a regulator regulating the power source; and (e) at least one beneficial agent reservoir associated with an electrode, wherein the regulator generates an initial load current necessary to provide a sought beneficial agent delivery rate and varies the load current to maintain a sought beneficial agent delivery rate as an apparent transport efficiency changes with time;

wherein the pattern of the change in said apparent transport efficiency is selected from group consisting of (a) $i_0 - K_{ATE}*t$, where $i_0$ is the initial load current and $K_{ATE}$ is a rate constant;

(b) $i_0 * \exp^{(-K_{ATE}*t)}$, where $i_0$ is the initial load current, $K_{ATE}$ is a rate constant, and t is time; and (c) function of the pH level of one of the electrodes.

* * * * *